United States Patent [19]

Axen

[11] 4,170,598
[45] Oct. 9, 1979

[54] 5-MERCURY DERIVATIVES OF 5,6-DIHYDROPROSTACYCLIN COMPOUNDS

[75] Inventor: Udo F. Axen, Plainwell, Mich.

[73] Assignee: The Upjohn Company, Kalamazoo, Mich.

[21] Appl. No.: 917,032

[22] Filed: Jun. 19, 1978

Related U.S. Application Data

[60] Division of Ser. No. 857,236, Dec. 5, 1977, Pat. No. 4,125,712, which is a continuation-in-part of Ser. No. 788,146, Apr. 19, 1977, abandoned, which is a continuation-in-part of Ser. No. 691,400, Jun. 1, 1976, abandoned.

[51] Int. Cl.² ........................................... C07D 307/93
[52] U.S. Cl. ............................... 260/346.22; 260/333; 260/345.7 P; 260/345.8 P; 260/346.73; 542/426; 542/429; 548/103; 548/252
[58] Field of Search .................. 260/346.22, 346.73, 260/308 A, 345.8 P, 345.7 P, 333; 542/426, 429

[56] References Cited
PUBLICATIONS
Johnson et al., J.A.C.S., 99:12, Jun. 8, 1977, pp. 4182–4184.

Primary Examiner—John M. Ford
Assistant Examiner—Bernard Dentz
Attorney, Agent, or Firm—Morris L. Nielsen

[57] ABSTRACT

Mercury derivatives of 5,6-dihydroprostacyclins are disclosed, illustrated for example by

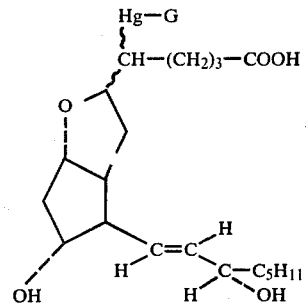

wherein G is nitrato, iodo, chloro, bromo, acetato, trifluoroacetato, or benzoato, and wherein ~ indicates alpha or beta configuration, said products having pharmacological activity.

10 Claims, No Drawings

5-MERCURY DERIVATIVES OF 5,6-DIHYDROPROSTACYCLIN COMPOUNDS

CROSS REFERENCE TO RELATED APPLLICATIONS

This is a division, of application Ser. No. 857,236, filed Dec. 5, 1977 now U.S. Pat. No. 4,125,712, which is a continuation-in-part of copending application Ser. No. 788,146 filed Apr 19, 1977, now abandoned which was a continuation-in-part of then copending applicaton Ser. No. 691,400 filed June 1, 1976 now abandoned.

BACKGROUND OF THE INVENTION

This invention relates to products having prostacyclin-like structure and to processes for preparing them. In particular this invention relates to 5-mercury derivatives of 5,6-dihydroprostacyclin compounds and to processes for preparing them.

The essential material for this application, including the background of the invention, the disclosure of the invention, and the description of the preferred embodiments, including Prepartions and Examples, is incorporated by reference from commonly owned U.S. Pat. No. 4,125,712, especially columns 33-34, 52-54, and 84-105, under the proviso of M.P.E.P. 608.01(p).

SUMMARY OF THE INVENTION

It is the purpose of this invention to provide novel products having pharmacological activity and utility as intermediates. It is a further purpose to provide processes for preparing these products and their intermediates.

The terms L, $Q_2$, etc. as used hereinafter are as defined in the Table of Definitions herein.

TABLE

Definition of Terms for Formulas

G is nitrato, iodo, chloro, bromo, acetato, trifluoroacetato, or benzoato.

L is (1) a valence bond, (2) —$(CH_2)_d$—wherein d is one to 5 inclusive, (3) —$(CH_2)_t$—$CF_2$—wherein t is 2, 3, or 4, (4)—$CH_2$—CH=CH—A—wherein A is a valence bond or —$(CH_2)_h$—wherein h is one, 2, or 3, or (5) —$CH_2$—O—$CH_2$—Y—wherein Y is a valence bond or —$(CH_2)_k$—wherein k is one or 2.

$Q_2$ is

wherein $R_3$ is hydrogen or alkyl of one to 4 carbon atoms, inclusive, and wherein $R_4$ is hydrogen, tetrahydropyran-2-yl, tetrahydrofuranyl, 1-ethoxyethyl or a group of the formula

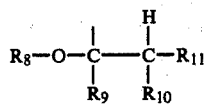

wherein $R_8$ is alkyl of one to 18 carbon atoms, inclusive, cycloalkyl of 3 to 10 carbon atoms, inclusive, aralkyl of 7 to 12 carbon atoms, inclusive, aralkyl of 7 to 12 carbon atoms, inclusive, phenyl, or phenyl substituted with one, 2, or 3 alkyl of one to 4 carbon atoms, inclusive, wherein $R_9$ and $R_{10}$ are the same or different, being hydrogen, alkyl of one to 4 carbon atoms, inclusive, phenyl or phenyl substituted with one, 2, or 3 alkyl of one to 4 carbon atoms, inclusive, or, when $R_9$ and $R_{10}$ are taken together, —$(CH_2)_a$—or —$(CH_2)_b$—O—$(CH_2)_c$—wherein "a" is 3, 4, or 5, b is one, 2, or 3, and c is one, 2, or 3 with the proviso that b plus c is 2, 3, or 4, and wherein $R_{11}$ is hydrogen or phenyl.

$R_3$ and $R_4$ are as defined above for $Q_2$.

$R_{22}$ is

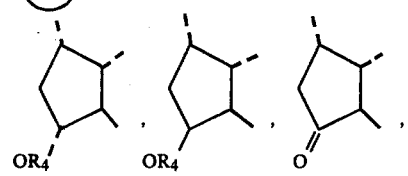

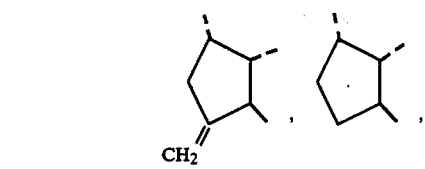

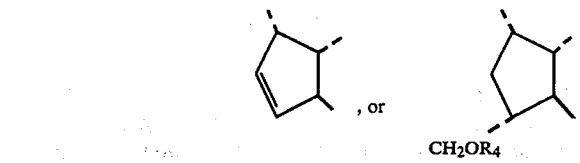

wherein $R_4$ is as defined above for $Q_2$.

$R_{25}$ is (1)

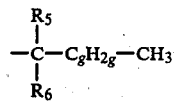

wherein $C_gH_{2g}$ is alkylene of one to 9 carbon atoms, inclusive, with one to 5 carbon atoms, inclusive, in the chain between —$CR_5R_6$—and terminal methyl, wherein $R_5$ and $R_6$ ar hydrogen, alkyl of one to 4 carbon atoms, inclusive, or fluoro, being the same or different, with the proviso that one of $R_5$ and $R_6$ is fluoro only when the other is hydrogen or fluoro;

(2)

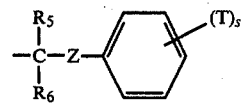

wherein $R_5$ and $R_6$ are as defined above with the proviso that neither $R_5$ nor $R_6$ is fluoro when Z is oza (—O—); wherein Z represents an oxa atom (—0—) or $C_jH_{2j}$ wherein $C_jH_{2j}$ is a valence bond or alkylene of one to 9 carbon atoms, inclusive, with one to 6 carbon atoms, inclusive between —$CR_5R_6$—and the phenyl ring; wherein T is alkyl of one to 4 carbon atoms, inclusive, fluoro, chloro, trifluoromethyl, or —$OR_7$—wherein $R_7$ is alkyl of one to 4 carbon atoms, inclusive, and s is zero, one, 2, or 3, with the proviso that not more than two T's are other than alkyl and when s is 2 or 3 the T's are either the same or different; or (3)

$$-CH_2\underset{H}{\overset{}{\diagdown}}C=C\underset{H}{\overset{CH_2CH_3}{\diagup}}.$$

$R_{30}$ is
(1) —COOR$_{19}$
(2) —CH$_2$OH
(3) —CH$_2$N(R$_{18}$)$_2$
(4)

$$-\overset{O}{\overset{\|}{C}}-N(R_{18})_2, \text{ or}$$

(5)

$$-C\underset{N-N}{\overset{NH-N}{\diagup\hspace{-0.2em}\diagdown}}$$

wherein $R_{19}$ is
(a) alkyl of one to 12 carbon atoms, inclusive,
(b) cycloalkyl of 3 to 10 carbon atoms, inclusive,
(c) aralkyl of 7 to 2 carbon atoms, inclusive,
(d) phenyl.
(e) phenyl substituted with one, 2, or 3 chloro or alkyl of one to 4 carbon atoms, inclusive, (f)

$$\text{—}\bigcirc\text{—NH—}\overset{O}{\overset{\|}{C}}\text{—}\bigcirc\text{—NH—}\overset{O}{\overset{\|}{C}}\text{—CH}_3,$$

(g)

$$\text{—}\bigcirc\text{—NH—}\overset{O}{\overset{\|}{C}}\text{—}\bigcirc,$$

(h)

$$\text{—}\bigcirc\text{—NH—}\overset{O}{\overset{\|}{C}}\text{—CH}_3,$$

(i)

$$\text{—}\bigcirc\text{—NH—}\overset{O}{\overset{\|}{C}}\text{—NH}_2,$$

(j)

$$\text{—}\bigcirc\text{—CH=N—NH—}\overset{O}{\overset{\|}{C}}\text{—NH}_2,$$

(k)

$$\text{—}\bigcirc\!\bigcirc,$$

-continued (l)

$$-\underset{R_{35}}{\overset{}{\text{CH}}}-\overset{O}{\overset{\|}{C}}-R_{34}$$

wherein $R_{34}$ is phenyl, p-bromophenyl, p-biphenylyl, p-nitrophenyl, p-benzamidophenyl, or 2-naphthyl, and wherein $R_{35}$ is hydrogen or benzoyl, (m) hydrogen; or (n) a pharmacologically acceptable cation; and wherein $R_{18}$ is hydrogen, alkyl of one to 12 carbon atoms, inclusive, benzyl, or phenyl, being the same or different.

$R_{36}$ is the same as $R_{30}$ except that it does not include salts in which $R_{19}$ of —COOR$_{19}$ is a pharmacologically acceptable cation.

X is trans—CH=CH—, cis—CH=CH—, —C≡C—, or —CH$_2$CH$_2$—.

The symbol ~ (wavy line) indicates attachment in alpha or beta configuration.

Accordingly there are provided mercury compounds of the formula

LXXXII $$\underset{}{R_{22}}\underset{\diagdown}{\overset{\diagup}{\bigcirc}}\underset{\underset{Q_2}{\overset{\|}{X-C-R_{25}}}}{\overset{O-CH\sim CH-L-R_{30}}{-CH_2}}\overset{Hg-G}{}$$

wherein G is nitrato, iodo, chloro, bromo, acetato, trifluoroacetato, or benzoato;

and wherein L, Q$_2$, $\bigcirc\!R_{22}$, R$_{25}$, R$_{30}$, X, and ~ are as defined above.

There are also provided mercury compounds of the formula

LXXXIII $$R_{22}\underset{\diagdown}{\overset{\diagup}{\bigcirc}}\underset{\underset{Q_2}{\overset{\|}{X-C-R_{25}}}}{\overset{O-CH\sim CH-L-\overset{O}{\overset{|}{C}}=O}{-CH_2}}\overset{Hg\text{—}O}{\overset{|}{}}$$

wherein L, Q$_2$, $\bigcirc\!R_{22}$, R$_{25}$, X, and ~ are as defined above.

The novel mercury compounds disclosed herein are useful for pharmacological purposes. They have antiprotozoal and antisyphilitic activity and are consequently effective in treating streptococci and staphylococci. They have antimicrobial activity and are useful for topical antiseptic treatment for animals, including humans, useful domestic animals, pets, zoological specimens, and laboratory animals. They are further useful in ophthalmiatrics.

For these purposes, these mercury compounds are preferably administered topically, for example in alcoholic solution at 0.002 to 0.01% concentration with a benzalkonium chloride as a preservative, or as a lotion, cream, or ointment in 0.5–5.0% concentration in combination with the usual pharmaceutically acceptable diluents. The exact application and concentration depends on such factors as the age, weight and condition of the subject.

Certain mercury compounds within the scope of formula XXXV are preferred for optimum biological response specificity, potency, and duration of activity. For example it is preferred that $Q_2$ be

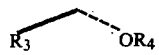

wherein $R_4$ is hydrogen; it is further preferred that L be trimethylene. When $R_3$ is alkyl, it is preferred that $R_3$ be methyl. Likewise, as to $R_{30}$, when $R_{19}$ in -COOR$_{19}$ is alkyl, it is preferred that $R_{19}$ be alkyl of one to 4 carbon atoms, especially methyl. Another preference is that G be chloro or acetato.

I claim:

1. A mercury compound of the formula

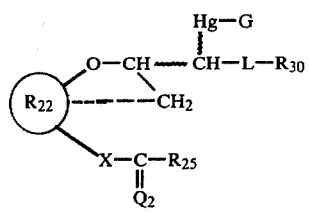

wherein G is nitrato, iodo, chloro, bromo, acetato, trifluoracetato, or benzoato;

wherein L is (1) a valence bond, (2) —(CH$_2$)$_d$—wherein d is one to 5 inclusive, (3) —(CH$_2$)$_t$—CF$_2$ wherein t is 2, 3, or 4, (4) —CH$_2$—CH=CH—A—wherein A is a valence bond or —(CH$_2$)$_h$—wherein h is one, 2, or 3, or (5) —CH$_2$—O—CH$_2$—Y—wherein Y is a valence bond or —(CH$_2$)$_k$—wherein k is one or 2; wherein $Q_2$ is

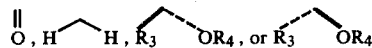

wherein $R_3$ is hydrogen or alkyl of one to 4 carbon atoms, inclusive, and wherein $R_4$ is hydrogen, tetrahydropyranyl, tetrahydrofuranyl, 1-ethoxyethyl or a group of the formula

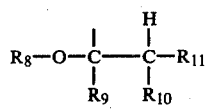

wherein $R_8$ is alkyl of one to 18 carbon atoms, inclusive, cycloalkyl of 3 to 10 carbon atoms, inclusive, aralkyl of 7 to 12 carbon atoms, inclusive, phenyl, or phenyl substituted with one, 2, or 3 alkyl of one to 4 carbon atoms, inclusive, wherein $R_9$ and $R_{10}$ are taken together, —(CH$_2$)$_a$— or —(CH$_2$)$_b$—O—(CH$_2$)$_c$—wherein a is 3, 4, or 5, b is one, 2, or 3, and c is one, 2, or 3 with the proviso that b plus c is 2, 3, or 4, and wherein $R_{11}$ is hydrogen or phenyl;

wherein $R_{22}$ is

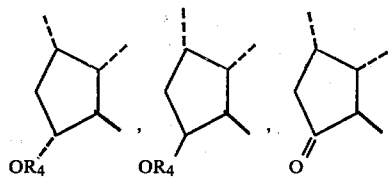

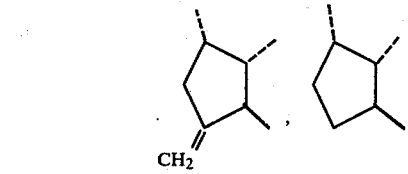

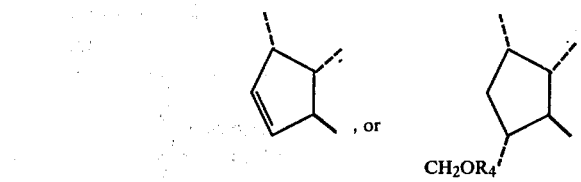

wherein $R_4$ is as defined above;
wherein $R_{25}$ is (1)

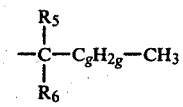

wherein $C_gH_{2g}$ is alkylene of one to 9 carbon atoms, inclusive, with one to 5 carbon atoms, inclusive in the chain between —CR$_5$R$_6$—and terminal methyl, wherein $R_5$ and $R_6$ are hydrogen, alkyl of one to 4 carbon atoms, inclusive, or fluoro, being the same or different, with the proviso that one of $R_5$ and $R_6$ is fluoro only when the other is hydrogen or fluoro;

(2)

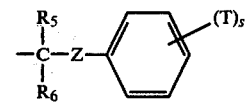

wherein $R_5$ and $R_6$ are as defined above with the proviso that neither $R_5$ nor $R_6$ is fluoro when Z is oxa (—O—); wherein Z represents an oxa atom (—O—) or $C_jH_{2j}$ wherein $C_jH_{2j}$ is a valence bond or alkylene of one to 9 carbon atoms, inclusive, substituted with zero, one, or 2 fluoro, with one to 6 carbon atoms, inclusive between —CR$_5$R$_6$—and the phenyl ring; wherein T is alkyl of one to 4 carbon atoms, inclusive, fluoro, chloro, trifluoromethyl, or —OR$_7$ wherein $R_7$ is alkyl of one to 4 carbon atoms, inclusive, and s is zero, one, 2, or 3, with the proviso that not more than two T's are other than alkyl and when s is 2 or 3 the T's are either the same or different; or (3)

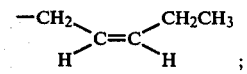

wherein $R_{30}$ is
(1) -COOR$_{19}$
(2) -CH$_2$OH
(3) -CH$_2$N(R$_{18}$)$_2$

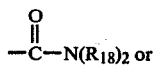 (4)

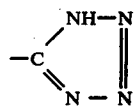 (5)

wherein $R_{19}$ is
(a) alkyl of one to 12 carbon atoms, inclusive,
(b) cycloalkyl of 3 to 10 carbon atoms, inclusive,
(c) aralkyl of 7 to 12 carbon atoms, inclusive,
(d) phenyl,
(e) phenyl substituted with one, 2, or 3 chloro or alkyl of one to 4 carbon atoms, inclusive;

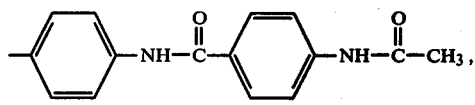 (f)

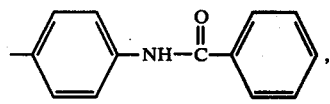 (g)

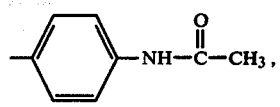 (h)

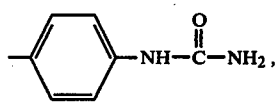 (i)

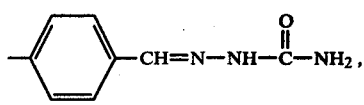 (j)

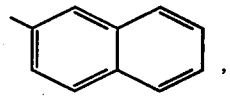 (k)

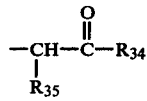 (l)

wherein $R_{34}$ is phenyl, p-bromophenyl, p-biphenylyl, p-nitrophenyl, p-benzamidophenyl, or 2-naphthyl, and wherein $R_{35}$ is hydrogen or benzoyl,
(m) hydrogen, or
(n) a pharmacologically acceptable cation; and wherein
$R_{18}$ is hydrogen, alkyl of one to 12 carbon atoms, inclusive, benzyl, or phenyl, being the same or different;

wherein X is trans—CH=CH—, cis—CH=CH—, —C≡C—, or —CH$_2$CH$_2$—; and wherein ~ indicates attachment in alpha or beta configuration.

2. 5-Chloromercurio-9-deoxy-6ξ,9α-epoxy-PGF$_1$, methyl ester, compounds according to claim 1.

3. A mercury compound of the formula

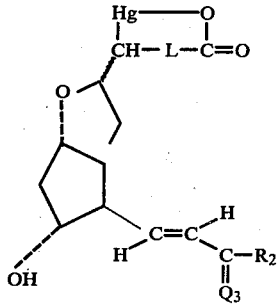

wherein L is —(CH$_2$)$_d$— or —CH$_2$O—CH$_2$—Y— wherein d is one to 5, inclusive, and Y is a valence bond or —(CH$_2$)$_k$—where k is one or 2; wherein R$_2$ is
(1)

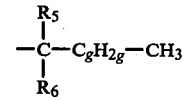

wherein C$_g$H$_{2g}$ is alkylene of one to 9 carbon atoms, inclusive, with one to 5 carbon atoms, inclusive, in the chain between —CR$_5$R$_6$—and terminal methyl, wherein R$_5$ and R$_6$ are hydrogen, alkyl of one to 4 carbon atoms, inclusive, or fluoro, being the same or different, with the proviso that one of R$_5$ and R$_6$ is fluoro only when the other is hydrogen or fluoro; or (2)

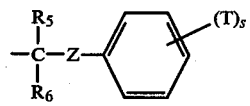

wherein R$_5$ and R$_6$ are as defined above with the proviso that neither R$_5$ nor R$_6$ is fluoro when Z is oxa (—O—); wherein Z represents an oxa atom (—O—) or C$_j$H$_{2j}$ wherein C$_j$H$_{2j}$ is a valence bond or alkylene of one to 9 carbon atoms, inclusive, with one to 6 carbon atoms, inclusive between —CR$_5$R$_6$—and the phenyl ring; wherein T is alkyl of one to 4 carbon atoms, inclusive, fluoro, chloro, trifluoromethyl, or —OR$_7$ wherein R$_7$ is hydrogen or alkyl of one to 4 carbon atoms, inclusive, and s is zero, one, 2, or 3, with the proviso that not more than two T's are other than alkyl and when s is 2 or 3 the T's are either the same or different; wherein Q$_3$ is

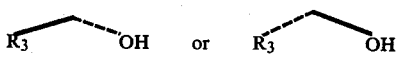

wherein R$_3$ is hydrogen or alkyl of one to 4 carbon atoms, inclusive; and wherein ~indicates attachment in alpha or beta configuration.

4. 5-Chloromercurio-9-deoxy-6ξ,9α-epoxy-PGF$_1$, methyl ester, less polar isomer, a compound according to claim 2.

5. 5-Chloromercurio-9-deoxy-6ξ,9α-epoxy-PGF$_1$, methyl ester, more polar isomer, a compound according to claim 2.

6. 5-Chloromercurio-9-deoxy-6ξ,9α-epoxy-17-phenyl-18,19,20-trinor-PGF$_1$, methyl ester, compounds according to claim 1.

7. 5-Chloromercurio-9-deoxy-6ξ,9α-epoxy-16,16-dimethyl-PGF$_1$, methyl ester, compounds according to claim 1.

8. 5-Chloromercurio-9-deoxy-6ξ,9α-epoxy-16-phenoxy-17,18,19,20-tetranor-PGF$_1$, compounds according to claim 1.

9. 5-Chloromercurio-9-deoxy-6ξ,9α-epoxy-PGF$_1$, compounds according to claim 1.

10. 5-Acetatomercurio-9-deoxy-6ξ, 9α-epoxy-PGF$_1$, methyl ester, compounds according to claim 1.

* * * * *

UNITED STATES PATENT OFFICE
CERTIFICATE OF CORRECTION

Patent No. 4,170,598          Dated 9 October 1979

Inventor(s) Udo F. Axen

It is certified that error appears in the above-identified patent and that said Letters Patent are hereby corrected as shown below:

Column 2, line 47, "ar hydrogen" should read -- are hydrogen --; line 62, "oza" should read -- oxa --.

Column 4, lines 26-34 and Column 5, lines 22-30, that portion of the formula reading

Column 5, line 63, "wherein $R_9$ and $R_{10}$ are taken together, $-(CH_2)_a-$" should read -- wherein $R_9$ and $R_{10}$ are the same or different, being hydrogen, alkyl of one to 4 carbon atoms, inclusive, phenyl or phenyl substituted with one, 2, or 3 alkyl of one to 4 carbon atoms, inclusive, or, when $R_9$ and $R_{10}$ are taken together, $-(CH_2)_a-$ --.

Column 8, line 22, "$-CH_2O-CH_2-Y-$" should read -- $-CH_2-O-CH_2-Y-$ --.

Signed and Sealed this

*Twenty-seventh* Day of *January 1981*

[SEAL]

*Attest:*

RENE D. TEGTMEYER

*Attesting Officer*      *Acting Commissioner of Patents and Trademarks*